United States Patent [19]

Granquist

[11] 3,976,744

[45] *Aug. 24, 1976

[54] LAMINAR HEAVY METAL ALUMINOSILICATES

[75] Inventor: William T. Granquist, Houston, Tex.

[73] Assignee: NL Industries, Inc., New York, N.Y.

[ * ] Notice: The portion of the term of this patent subsequent to Dec. 3, 1991, has been disclaimed.

[22] Filed: Sept. 23, 1974

[21] Appl. No.: 508,339

Related U.S. Application Data

[63] Continuation-in-part of Ser. No. 291,252, Sept. 22, 1972, Pat. No. 3,852,405.

[52] U.S. Cl. ............................... 423/118; 423/328; 252/455 R; 208/120
[51] Int. Cl.² .................. C01B 33/26; C01B 33/28; B01J 29/06
[58] Field of Search ................ 252/455 R; 423/118, 423/328; 208/120

[56] References Cited
UNITED STATES PATENTS
3,852,405    12/1974    Granquist.......................... 252/455 R Primary Examiner—Carl F. Dees
Attorney, Agent, or Firm—Delmar H. Larsen; Roy F. House; Robert L. Lehman

[57] ABSTRACT

Laminar 2 : 1 layer-lattice aluminosilicate minerals containing intra-lattice multivalent ions such as nickel, copper, cobalt and others. The minerals are particularly useful in catalytic operations. Procedures for preparing the inventive minerals are given.

15 Claims, No Drawings

LAMINAR HEAVY METAL ALUMINOSILICATES

This application is a continuation-in-part of my copending application Ser. No. 291,252, filed Sept. 22, 1972 U.S. Pat. No. 3,852,405, and entitled "Laminar Heavy Metal Aluminosilicates".

This invention relates to nickel aluminosilicates, and more particularly to a novel group of mixed layer laminar heavy metal aluminosilicates and to their employment in catalytic reactions.

Compounds of alumina and silica of the most diverse types not only occur in nature but have been variously compounded and synthesized, and have been found to have varying degrees of catalytic activity for such reactions as hydrocarbon cracking, hydrocarbon reforming, various organic syntheses and conversions, and the like. The make-up of this very broad class of substances varies not only with respect to compositions, but with respect to crystallinity, and encompasses such members as relatively amorphous silica-alumina cracking catalysts, relatively well crystallized acid-activated clays, highly crystalline zeolite minerals, both natural and synthesized, and others. A particular type furnishing a background for the present invention is that described in U.S. Pat. No. 3,252,757, issued May 24, 1966, and describing a mixed layer laminar silicate mineral, which has been found to have utility as a catalyst for many kinds of catalytic reactions.

Because of the very broad range of possible sustances derived primarily from alumina and silica, it is not surprising that research in this broad field over nearly a century continues to yield novel types with, in some cases, surprising and unexpected properties, with suitability for particular reactions not shared by other members of the broad group.

An object of the present invention is to provide a novel group of heavy metal aluminosilicates and processes for making them.

Another object of the invention is to provide a novel group of aluminosilicate catalysts, having useful catalytic characteristics description thereof proceeds.

Generally speaking and in accordance with illustrative embodiments of my invention, I provide a synthetic laminar 2:1 layer-lattice aluminosilicate mineral possessing an inherent negative charge balanced by cations exterior to said lattice and corresponding to the following formula for a given embodiment:

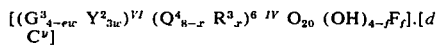

where $2 \leq e < 3$ $0 \leq w \leq 2$ $0 \leq ew \leq 4$ $0 \leq (e-2)w \leq \frac{1}{3}$ $0.05 \leq x < 2$ $f \leq 4$ $0.05 \leq dy \leq 2$ wherein said first bracket represents the average unit cell formulation of said layer-lattice and said second bracket represents said charge balancing cations; and wherein G is selected from the class consisting of trivalent cations having an ionic radius not to exceed 0.75 A and mixtures thereof, provided that G is less than 100 mole percent Al when $w = 0$;

Y is selected from the class consisting of divalent cations having an ionic radius not to exceed 0.75 A and mixtures thereof; provided that Y is less than 100 mole percent Mg when $w = 2$;

Q is at least 95 mole percent silicon ions the remainder consisting of tetravalent cations having an ionic radius not to exceed 0.64 A;

R is selected from the group consisting of trivalent cations having an ionic radius not to exceed 0.64 A and mixtures thereof; and C is at least one charge-balancing cation, with y being its valence and d being the number of such cations C where:

$$dy = x + 3(e-2)w.$$

In the above statement of the nature of G, Y, Q, and R, it will be noted that those substituents other than aluminum and silicon are designated in terms of ionic radius and ionic charge.

It is further clear from the formulation given that G, while consisting predominantly of aluminum ions, may include a minor proportion of trivalent ions isomorphously substituted for some of the aluminum ions without affecting the overall charge; and that Y consists of divalent metallic ions either isomorphously substituted for a like number of aluminum ions, whereby a charge deficit results, or substituted on the basis of three divalent ions for two aluminum trivalent ions with no resulting charge deficit, or a mixture of both. In like manner, it is clear that Q, while consisting predominantly of silicon ions, may include a minor proportion of tetravalent ions isomorphously substituted for some of the silicon ions without affecting the overall charge; while R consists of trivalent ions isomorphously substituted for some of the silicon ions without affecting the overall charge; while R consists of trivalent ions isomorphously substituted for a like number of silicon ions, whereby a charge deficit results from the substitution of a trivalent ion for a tetravalent ion.

The specific elements which are included in the above formulation other than aluminum and silicon are relatively small in number, because of the limitations imposed by the stipulated ionic charge and ionic radius.

For the sake of convenience, a tabulation follows in which the elements usable in accordance with the invention are listed. It will be clear that this listing results from checking each element against its known valence states and its known ionic radius for each applicable valence state, taking into account the coordination number where the latter affects the ionic radius. Tables of ionic radius for various elements have appeared in the literature during the last half century, and in the case of disparity among the values given for a specified element, the best value has been chosen in the light of all of the known data, and this best value is the one which appears in the tables which follow.

| G: Trivalent - Maximum 0.75 A | |
|---|---|
| Aluminum (Al) | 0.50 |
| Chromium (Cr) | 0.64 |
| Manganese (Mn) | 0.62 |
| Iron (Fe) | 0.60 |
| Cobalt (Co) | 0.63 |

-continued

|  |  |
|---|---|
| Gallium (Ga) | 0.62 |
| Rhodium (Rh) | 0.68 |
| Scandium (Sc) | 0.73 |
| Y: Divalent - Maximum 0.75 A | |
| Beryllium (Be) | 0.31 |
| Iron (Fe) | 0.75 |
| Magnesium (Mg) | 0.65 |
| Nickel (Ni) | 0.69 |
| Cobalt (Co) | 0.72 |
| Copper (Cu) | 0.72 |
| Zinc (Zn) | 0.74 |
| Q: Tetravalent - Maximum 0.64 A | |
| Silicon (Si) | 0.41 |
| Germanium (Ge) | 0.53 |
| R: Trivalent - Maximum 0.64 A | |
| Aluminum (Al) | 0.50 |
| Chromium (Cr) | 0.64 |
| Manganese (Mn) | 0.62 |
| Iron (Fe) | 0.60 |
| Cobalt (Co) | 0.63 |
| Gallium (Ga) | 0.62 |

Returning now to the formulation given hereinabove, the first bracket represents the laminar layer-lattice unit cell formulation, which as was explained hereinabove possesses an inherent negative charge by reason of the fact that the positive charges of the cations are less than the negative charges of the anions. Since the inventive preparation as a whole is electrostatically neutral, the charge-balancing cations which are necessarily present are external to the lattice and are represented by the second bracket, in which C stands for the charge balancing cations taken as a whole, with $y$ being their average charge and $d$ being the number of chargebalancing cations per unit cell. It will be recognized that in this formulation, C may actually correspond to a large variety of charge-balancing cations simultaneously present, such as for example a mixture of hydrogen, sodium, calcium, and the like cations.

In accordance with a more particular formulation, the composition of the charge-balancing cations in the second bracket may conveniently be represented as follows:

$$[a\ M^n + b\ Al(OH)_{3z}]^{z\ 3-z}$$

wherein $$an + bz = dy = x + 3(e-2)w$$

and $M$ is selected from the group consisting of hydrogen, ammonium, alkali metal cations, multivalent metal cations other than aluminum, and partial hydroxides of multivalent metal cations, and $n$ is the unsatisfied valence of $M$.

As will become apparent from the further description of my invention, this second, more particular characterization of the charge-balancing cations corresponds more closely to the products initially obtained in accordance with my preferred mode of preparation. Moreover, it provides explicitly for any hydroxyaluminum cations which may be present. It will be understood that such hydroxyaluminum cations are commonly present as a mixture of species, as described for example in U.S. Geological survey Water-Supply Paper 1827-A (1967), which is incorporated herein by reference. However, since these charge-balancing cations are essentially exchangeable without disturbing the lattice itself, the latter being represented by the first bracket, after having made a given preparation in accordance with the invention by a preferred procedure, it is relatively simple to exchange a portion or indeed substantially all of the cations in the second bracket for some other preselected cation or mixture of cations. Thus, for example, referring to the first general formulation given hereinabove, the chargebalancing cation C can at will be selected from such diverse species as lithium, rubidium, palladium, hydroxyaluminum, hydroxynickel, trimethylammonium, alkyl phosphonium, and the like cations and indeed mixtures thereof. Thus, C may be selected from the group consisting of alkali metal, alkaline earth metal, heavy metal, heavy metal partial hydroxide, ammonium, substituted ammonium, substituted phosphonium, and the like cations and mixtures thereof.

Those skilled in the art will recognize, accordingly, that the first bracket of the above formula relates to a fixed array of ions in a tripartite lamina which for convenience may be described as muscovite-like, and in which the positive ions shown in the first parenthesis are in octahedral coordination with sheets comprising oxygen, hydroxyl, and fluoride ions; whereas the positive ions shown in the second parenthesis in the first bracket are in tetrahedral coordination jointly with the aforesaid sheets of oxygen, hydroxyl, and fluoride ions, and also with sheets of oxygen ions in essentially a hexagonal ring array, constituting the external faces of the tripartite lamina. The positive ions shown in the second bracket have no essentially fixed position, but are in effect external to the lattice of the tripartite lamina.

Those skilled in the art will also recognize that when some of the parameters in the above formulations have values outside of the stipulated ranges, the formulations reduce to representations of various end members of a broad group of laminar aluminosilicates, which of course are outside of the scope of the present invention. Thus, for example, when $w$ and $x$ both equal zero, and no fluoride ion is present, the first bracket describes the mineral pyrophyllite. From the first equation set forth under the formula, it will be seen that the factor $d$ is equal to zero, so that the ionic species set forth in the second bracket are not present, which of course results from the fact that the lattice of pyrophyllite is charge-balanced. Again, for the case in which $x$ equals zero, $w$ equals two, $e$ equals two, and no fluoride is present, a mineral results in which the lattice is likewise chargebalanced, and the ionic species set forth in the second bracket are not present. Such a mineral is described in U.S. Pat. No. 2,658,875, to Cornelis et al.

In general, 2 : 1 layer-lattice aluminosilicate minerals or in alternative nomenclature, tripartite aluminosilicate minerals of the type concerned in the present invention, may be classified as either dioctahedral or trioctahedral, depending upon whether the number of cations per unit cell in the octahedral (or inner) layer is approximately 4 or 6 respectively. The foregoing structural formula is as stated an overall formula for a given preparation, and the fact that the number of such octahedral cations may vary from 4 to 6 in a continuous manner in the formulation given does not mean that a single lamina is present having such an intermediate number of cations. In point of fact, the individual laminae are believed to be either dioctahedral or trioctahedral, and in a given preparation the relative portions of the dioctahedral and trioctahedral species will give rise to the numerical values obtained in quantitatively characterizing the preparation in accordance with the foregoing formula. Where $e$ in the formulation is intermediate between 2 and 3, accordingly, both 1 : 1 and 3 : 2 substitutions are present. Because of the extremely small particle size of the minerals in accordance with the invention, the exact physical nature of these mixed phase systems is uncertain. In any case, the products in accordance with the invention which are produced by simultaneously synthesizing both phases in place in a single reaction mixture to produce a mixed-phase mineral differ significantly from compositionally similar mixtures obtained by simply mixing together the separately synthesized dioctahedral and trioctahedral members.

It may be emphasized that each product made in accordance with the invention is a simple mineral species, even though it may contain two phases, because in the latter cases the phases are believed to be interlaminated on a scale substantially that of the individual layer lattices. Any naturally occurring clay exhibiting this construction is generally referred to as a mixed-layer mineral.

The minerals in accordance with the invention are synthesized by a hydrothermal route, detailed examples of which will be given later. The procedure follows in a general way that set forth in the aforementioned U.S. Pat. No. 3,252,757, except that the cited patent does not relate to the inventive aluminosilicates, which contain additional elements, so that the reaction mixtures required in the present invention are substantially different. As will be evident from the structural formula already given, the reaction mixture of the hydrothermal synthesis includes a source of one or more multivalent cations other than aluminum and silicon. For example, for the case of nickel, this may be a relatively soluble compoundm such as for example, nickel acetate, nickel fluoride, nickel nitrate, and the like; or it may be a relatively insoluble nickel compound such as nickel hydroxide. It is of interest that in general the inclusion of soluble nickel salts in the reaction mixture tends to cause the nickel to occur predominantly in the trioctaheral phase, while relatively insoluble nickel compounds promote its occurence in the dioctahedral phase. The terms are well understood in the art, and a brief explanation in addition to that already given may be found on page 156 of the book by George Brown "The X-Ray Identification and Crystal Structures of Clay Minerals", London 1961. The classical paper by Ross and Hendricks "Minerals of the Montmorillonite Group", U.S. Geological Survey Professional Paper 205-B (1945) is helpful, particularly for its treatment of variation of the members of a given series of laminar aluminosilicate minerals.

For the other elements useful in practising the invention, such as cobalt, gallium, copper, zinc, iron, manganese, and so forth, as more fully listed hereinabove, the most commonly available simple inorganic and organic compounds thereof may in general be used, as will be evident to those skilled in the art. Specific examples will be given later.

Some specific examples of the synthesis of heavy metal aluminosilicates in accordance with the invention will now be given. From these examples, the general procedure will be clear. It may be noted that if one desires a higher or lower ratio of some particular selected heavy metal to silicon, or a higher or lower ratio of aluminum to silicon in the final product, the relative proportions of these components in the reaction mixture should be adjusted accordingly. The various specific examples illustrate this.

For the sake of an orderly presentation of the examples, the first ones which follow illustrate the practice of the invention where nickel is the sole multivalent lattice cation besides aluminum and silicon. Later examples show other heavy metals and mixtures thereof.

Examples A and B are of interest as illustrating the effects of using a relatively insoluble nickel source on the one hand, as in Example A, and of using a relatively soluble nickel source on the other, as in Example B.

In Example A, the nickel occurs predominantly in the dioctahedral phase where it proxies for $Al^{+++}$. In Example B. the nickel is predominantly in the trioctahedral phase. In both examples, more dioctahedral phase is present than trioctahedral, although more so in the case of Example A. These examples follow:

EXAMPLE A

Forty grams of commercial silicic acid (Fisher), assaying 79% $SiO_2$, were dispersed in one liter of distilled water. To this dispersion were added, with stirring, 70.8 g of $AlCl_3.6H_2O$ and 17.6 g $NiCl_2.6H_2O$. When solution of these chlorides was complete, 75 ml of aqua ammonia (29% $NH_3$) were then added to precipitate the hydroxides. The slurry was filtered and washed three times with water by reslurrying and refiltration. The final cake was dispersed in water, 3.0 g NaOH (previously dissolved in a small amount of water) added, and the slurry made up to one liter.

This slurry was placed in a Type 347 stainless steel Aminco superpressure bomb, with an inside diameter of 2 9/16 inches and an inside depth of 21 inches, equipped with a standard Aminco closure. Heating and stirring were furnished by a standard Aminco heating jacket mounted on a rocker assembly. The jacket temperature was controlled by an off-on device. The bomb was vented, at the boiling point of the contents and without rocking, until the air had been displaced from the vessel. The vent was then closed, rocking started, and the temperature allowed to climb to the control point, 285°C. At the end of the scheduled reaction time of 48 hours, heating was discontinued, and the autoclave and contents allowed to cool, with continued rocking. The product slurry, which had a pH of 6, was filtered and the cake redispersed in aqua ammonia and refiltered twice, followed by one such treatment with distilled water. The final filter cake was dried at 110°C. It is estimated that in the final product, the unit cell parameters were $w = ⅓$ (or?1 Ni/u.c.) and $x = 0.8$ (i.e., up to 0.8 Al IV/u.c.), depending on the distribution of Al between the IV-sites and the charge-balancing hydroxyaluminum species.

EXAMPLE B 346 g of hydrated alumina, $Al_2O_3.3H_2O$ (Alcoa C 31, 64.9% $Al_2O_3$) were added with stirring to a polysilicic acid sol which was prepared by passing sodium silicate solution over hydrogenresin. The volume of sol was chosen so as to contain 317 g $SiO_2$. 8.95 g of $NH_4F.HF$ were then dissolved in this silicaalumina slurry. In a separate vessel, 19.1 g of $NiF_2.4H_2O$ were dispersed in 63.0 g of an ammonium hydroxide solution assaying 58.8% $NH_4OH$. This ammoniacal slurry was then added to the silica-alumina dispersion, with stirring. If gel formation occurred, sufficient water was added to break the gel so that efficient stirring could continue. The final feed slurry, with a pH = 8.5, was charged to a 1-gallon stirred autoclave, heated quickly (1 - 1½ hr.) until pressure line-out at 1240 psig (300°C), and maintained at this T,P condition for 3 hours. The product was cooled in the pressure vessel, removed, sheared in a blender to insure homogeneity, and a small quantity dried for analysis. The product slurry had a pH = 7.4. The dried sample had a total nickel content of 1.30% (as Ni); the non-exchangeable Ni content was 1.2%. The sample gave an X-ray diffraction pattern typical of 2:1 layer-lattice silicates.

Pd was placed on the clay by adding to 1535 g of product slurry a solution which contained 4.185 g of $(NH_4)_2PdCl_4$ dissolved in 125 ml of deionized water. The slurry was stirred (with mild agitation) overnight at room temperature, and then filtered. The filter cake was washed twice by redispersion in deionized water and refiltration. The final filter cake was air-dried at 110°C, cooled, and crushed to 10/20 mesh particles. The final catalyst contained 1.4% Ni and 0.8% Pd.

EXAMPLE C

This synthesis was similar to Example B, described above, except that the proportions of the starting materials were altered to yield a clay of approximately 10% Ni content. The feed slurry was composed of 2890 g of polysilicic acid sol (which contained 5.2% $SiO_2$), 164 g $Al_2O_3.3H_2O$, 95.5 g $NiF_2.4H_2O$ and 42.7 g of $NH_4OH$ solution (which contained 47% $NH_4OH$). The feed and product pH were 8.4 and 85 respectively. The total nickel content of the product was 11.1% (as Ni); the non-exchangeable nickel content was 9.9%. Pd was added as previously described; the finished catalyst contained 10.1% Ni and 0.8% Pd.

EXAMPLE D 25 pounds of $SiO_2$ (as polysilicic acid sol assaying 5.2% $SiO_2$) were pumped into a feed mix tank equipped with an efficient high-torque stirring system. To this silica sol were added with stirring 27.3 pounds commercial trihydrate of alumina (which assayed 64.9% $Al_2O_3$), 23.5 pounds of nickel acetate.4-hydrate (which contained 23.7% Ni) previously dissolved in 10 gal $H_2O$ and 1.24 pounds of $NH_4F.HF$ (purity of 96%) already in solution in one gal $H_2O$. With continued stirring, sufficient aqua ammonia was added to bring the slurry pH to 8. This pH adjustment was accomplished with 13 pounds of aqua ammonia, which contained 48% $NH_4OH$. The final volume of slurry was about 75 gal.

After approximately 10 hr. of agitation, the feed slurry was pumped into a 100 gal jacketed autoclave, heated by electric heaters immersed in Dowtherm. The autoclave was sealed and heating started. After 12hr-45 min., temperature lined out at 300°C and a pressure of 1240 psig. The contents were maintained at these conditions for 4 hrs at which time drawdown through a quench condenser and expansion valve was started. Total time for discharge was 1 hr. A small sample was dried, examined and found to be a 2:1 layer-lattice aluminosilicate which contained 9.6% Ni. A portion of the product was retained as slurry for after-treatment by Pd impregnation as previously described.

EXAMPLE E 260 gms of nickel acetate 4-hydrate ($NiAc_2.4H_2O$) were dissolved in 500 ml of deionized water and added, with stirring, to a sufficient quantity of polysilicic acid sol (assay: 5.2% $SiO_2$) to contain 150 gms of $SiO_2$. With continued stirring, 7.45 gm of $NH_4F.HF$ (purity: 96%) and 33.3 gm of aqua ammonia (47% $NH_4OH$) were added, in the order given. The resultant mixture was placed in a 1-gal stainless steel stirred autoclave and heated quickly (1 ½ hrs) to 300°C and 1240 psig. The contents were maintained at these conditions for 4 hours. Heating was then discontinued and the product slurry cooled in the pressure vessel, removed, and oven-dried at 110°C.

While the products in accordance with the invention are well crystallized, the actual size of the crystal does not lend itself readily to characterization by the older methods of optical crystallography. Much more precise are the results obtained by x-ray diffraction, and by way of further characterization of the products in accordance with the invention, there follow tabulations of spacings and intensities obtained on a number of products in accordance with the invention. Tables I–IV inclusive show such x-ray diffraction data for two series of products made along the lines indicated in Examples B – E inclusive.

The products tabulated in Table I consist, except at the end members, of mixed di- and trioctahedral phases. The Ni-free end member is "pure" dioctahedral; the $Ni_6$ sample is "pure" trioctahedral. In the intermediate range, the amount of trioctahedral phase increases with the Ni/unit cell. The products summarized in Table III are "pure" trioctahedral.

In the series shown in Tables I and II, the aluminum content was held constant at one and one half atoms per unit cell while the nickel content was varied from zero to six atoms per unit cell. A summary of the results obtained is given in Table I, with a more detailed tabulation in Table II. It will be understood that the first member of this series, in which no nickel is present at all is outside of the scope of the invention; the results are shown merely for comparative purposes.

In the series for which results are given in Tables III and IV, the nickel content was held constant at six atoms per unit cell, while the tetrahedral aluminum was varied from zero to two atoms per unit cell. Here again, the first member of the series, containing no aluminum, is outside of the scope of this invention and the results are included in the tabulation for comparative purposes. Table III is a summary, and Table IV shows the results in detail for each member of the series.

TABLE 1

SUMMARY
Ni VARIABLE, x = 1.5
d,A

| Index* | Ni/u.c.:0 | ⅛ | 1 | 2 | 3 | 4 | 5 | 6 |
|---|---|---|---|---|---|---|---|---|
| 001 | | | | | | | | |
| 001 | 10.6 | 11.8 | 11.3 | 11.3 | 13.0[b] | 13.4[b] | 13.4[b] | 13.6[b] |
| 002 | 5.18 | 5.68 | 5.34 | 5.24 | — | — | — | — |
| 003 | 3.41 | 3.26 | 3.37 | 3.34 | — | — | — | — |
| 004 | — | — | — | — | 3.30 | 3.26 | 3.24 | 3.29 |
| 005 | 2.061 | 2.065 | — | — | — | — | — | — |
| hk | | | | | | | | |

TABLE 1-continued

SUMMARY
Ni VARIABLE, x = 1.5

| Index* | Ni/u.c.:0 | ⅛ | 1 | 2 | 3 | 4 | 5 | 6 |
|---|---|---|---|---|---|---|---|---|
| | | | | d,A | | | | |
| 11;02 | 4.46 | 4.46 | 4.50 | 4.48 | 4.48 | 4.50 | 4.55 | 4.5 |
| 13;20 | 2.57 | 2.56 | 2.58 | 2.57 | 2.58 | 2.58 | 2.61 | 2.5 |
| 31;15;24 | 1.691 | 1.687 | 1.699 | 1.67 | 1.691 | — | — | — |
| 06 | 1.499 | 1.492 | 1.517)$^a$ | 1.522)$^a$ | 1.520)$^a$ | 1.522 | 1.524 | 1.5 |
| | | | 1.502) | 1.502) | 1.500) | | | |
| hkl | | | | | | | | |
| 131(Prob.) | 2.453 | 2.45 | 2.453 | 2.42 | 2.466 | 2.47 | — | 2.5 |

*Significant peaks only. See detailed tables for intensity data. Basal sequence may involve mixed layering. If so, indices would be mixed; e.g. 003/004.
$^a$Doublet consisting of di- and trioctahedral components.
$^b$Probably intercalated acetate

TABLE II

Ni VARIABLE, x = 1.5 (BASED ON STARTING COMPOSITION)

Ni = ⅛u.c.

| d,A | Probable Index | Height, mm | | Comment |
|---|---|---|---|---|
| 11.8 | 001/001 | 172 | | Strong, Symmetrical |
| 5.68 | 002/002(?) | 18 | | Weak, Symmetrical |
| 4.46 | 11;02 | 148 | 5.5 mm,w/2* | Strong, Asymmetrical |
| 3.26 | 003/004 | 48 | | Symmetrical |
| 2.56 | 13;20 | 65 | | Asymmetrical(band,2.31–2.62 |
| 2.45 | hk | 36 | | Shoulder |
| 2.065 | 00(?) | 18 | | Symmetrical |
| 1.687 | 31;15;24 | 20 | | Asymmetrical |
| 1.492 | 06 | 42 | 12mm, w at h/2** | Slightly Assymetrical |

*w/2 = half-width at baseline. For asymmetrical peak, smaller distance
**w at h/2 = width at half-height

Ni = 1/u.c.

| d,A | Probable Index | Height, mm | | Comment |
|---|---|---|---|---|
| 11.32 A | 001/001 | 140 | | Strong, well defined |
| 5.34 | 002/002 | 11 | | Weak, Symmetrical |
| 4.50 | 11;02 | 147 | 7.5 mm w/2 | Asymmetrical, Sharp |
| 3.37 | 003/004(?) | 47 | | Symmetrical, broad |
| 2.583 | 13;20 | 102 | | Asymmetrical, Mod. sharp |
| 2.453 | hk | 56 | | Symmetrical (?) |
| 1.699 | 31;15;24 | 17 | | Asymmetrical, broad |
| 1.517) | 06 | 22 | | (Doublet — 1.517 is |
| 1.502) | | 48 | | (a shoulder on low-angle |
| | | | | (side of 1.502 |

Ni = 2/u.c.

| d,A | Probable Index | Height, mm | | Comment |
|---|---|---|---|---|
| 11.32 | 001/001 | 135 | | Not well-defined |
| 5.24 | 002/002 | 6 | | Symmetrical |
| 4.48 | 11;02 | 122 | 6mm w/2 | Strong, sharp, asymmetrical |
| 3.34 | 003/004 | 40 | | Symmetrical, broad |
| 2.57 | 13;20 | 93 | | Asymmetrical, Mod. sharp |
| 2.42 | hk | 55 | | Asymmetrical |
| 1.67 | 31;15;24 | 13 | | |
| 1.522) | 06 | 35 | (Doublet — about equal | |
| 1.502) | | 35 | | (height; trioct. dioct. |

Ni = 3/u.c.

| d,A | Probable Index | Height, mm | | Comment |
|---|---|---|---|---|
| 13.0 | 001/001* | 190 | | May have intercalated acetate |
| 4.48 | 11;02 | 90 | 11mm w/2 | Asymmetrical |
| 3.30 | 003/004* | 40 | | Broad, symmetrical |
| 2.576 | 13;20 | 96 | | Mod. sharp, asymmetrical |
| 2.466 | hk | 61 | | Ill-defined |
| 1.691 | 31;15;24 | 15 | | Broad |
| 1.520) | 06 | 53 | | (Doublet — 1.500 A a shoulder |
| 1.500) | | | | (on high angle side of 1.520 |
| | | | | (trioct. |

*Uncertain due to complications due to mixed layers.

Ni = 4/u.c.

| d,A | Probable Index | Height, mm | | Comment |
|---|---|---|---|---|
| 13.4 A | 001/001* | 201 | | Ill-defined — may have intercalated acetate |
| 4.50 | 11;02 | 56 | 14mm w/2 | Asymmetrical |
| 3.26 | 00 | 38 | | Broad, symmetrical |
| 2.58 | 13;20 | 86 | | Asymmetrical |
| 2.47 | hk | 58 | | Broad shoulder on 2.58 |
| 1.522 | 06 | 67 | | Asymmetrical — tailing toward high angle side |

TABLE II-continued

Ni = 5/u.c.

| d,A | Probable Index | Height, mm | | Comment |
|---|---|---|---|---|
| 13.4 | 001 | 200 mm | | Uncertain height — not well defined |
| 4.55 | 11;02 | 58 mm | 9 mm w/2 | Asymmetrical |
| 3.24 | 00 | 45 | | Symmetrical |
| 2.61 | 13;20 | 90 | | Asymmetrical — band head band extends 2.64 1.97 |
| 1.524 | 06 | 87 | | Asymmetrical — tails toward high angle side |

*Uncertain due to complications due to mixed layers.

Ni = 6/u.c.

| d,A | Probable Index | Height, mm | | Comment |
|---|---|---|---|---|
| 13.6 | 001* | 192 | | Poorly defined — may be intercalated acetate |
| 4.54 | 11;02 | 59 | 9 mm w/2 | Asymmetrical |
| 3.29 | 004* | 40 | | Very broad, symmetrical |
| 2.58 | 13;20 | 83 | | Broad, band-head of band extending from 2.64 1.97 A |
| 2.51 | hk | 84 | | Part of above band |
| 1.522 | 06 | 98 | 14mm, width at h/2 | Mod. sharp asymm. tailing to high angle side |

*Uncertain due to complications due to mixed layers.

TABLE III

SUMMARY
Ni = 6, x = VARIABLE
$Al^{IV}$/u.c.

| Index* | 0 | ½ | 1 | 1.5 | 2 |
|---|---|---|---|---|---|
| ool | | | | | |
| 001 | 9.6 | 11.6 | 13.4$^a$ | 13.6 | — |
| 002 | — | — | — | — | — |
| 003 | 3.145 | — | — | — | — |
| 004 | — | 3.25 | 3.32 | 3.29 | 3.42 |
| 005 | — | — | — | — | — |
| hk | | | | | |
| 11;02 | 4.55 | 4.55 | 4.56 | 4.54 | 4.53 |
| 13;20 | — | 2.62 | 2.59 | 2.58 | 2.62 |
| 22;04 | 2.27 | — | — | — | — |
| 31;15;24 | — | — | — | — | — |
| 06 | 1.522 | 1.522 | 1.524 | 1.522 | 1.526 |
| hkl | | | | | |
| 131(prob) | 2.51 | — | — | 2.51 | 2.51 |

*Significant peaks only. See detailed tables for intensity data. Basal Sequence may involve mixed-layering. If so, indices would be mix e.g., 003/004. Also, possible intercalation of acetate may affect 00
$^a$This particular sample, when oriented and glycol treated, gave an 001 of 17.7 A.

TABLE IV

Ni 6, x VARIABLE x 2.0 (expectation value)

| d,A | Probable Index | Height, mm | | Comment |
|---|---|---|---|---|
| 4.53 | 11;02 | 48.5 | | Asymmetrical |
| 3.42 | 004* | 46 | | Broad, symmetrical |
| 2.62 | 13;20 | 83 | 14 mm, w/2 | Very broad, part of band extending from 2.64 A 1.97 |
| 2.51 | hk | 85 | | V. broad; part of same band. |
| 1.526 | 06 | 78 | 16 mm, w at h/2 | Moderately sharp; slightly asymmetric. |

NOTE: 001 is not defined; slight trace of kaolinite-like phase at 7.08 A.

x 1.5 (expectation value)

| d,A | Probable Index | Height, mm | | Comment |
|---|---|---|---|---|
| 13.6 | 001 | 192 | | Poorly defined. |
| 4.54 | 11;02 | 59 | 9 mm, w/2 | Asymmetrical |
| 3.29 | 004* | 40 | | Very broad, symmetrical |
| 2.58 | 13;20 | 83 | | Broad; part of band extending from 2.64 1.97 A |
| 2.51 | hk | 84 | | |
| 1.522 | 06 | 98.5 | 14 mm, w at h/2 | Moderately sharp; slightly asymmetric |

*Uncertain due to complications due to mixed layers.

x 1.0 (expectation value)

| d,A | Probable Index | Height, mm | | Comment |
|---|---|---|---|---|
| 13.4 (expanded to 17.7 A w/glycol treatment) | 001 | 191 | | Well-defined on oriented slide; poorly-defined on random slide. |
| 4.56 | 11;02 | 61 | 11 mm, w/2 | Asymmetrical |
| 3.32 | 004* | 41 | | Very broad, symmetrical |
| 2.59 | 13;20 | 83 | | Asymmetrical band extending |

TABLE IV-continued

| 1.524 | 06 | 90 | 14 mm, w at h/2 | from 2.661  1.97<br>Moderately sharp; slightly asymmetric. | x 0.5 (expectation value)

| d,A | Probable Index | Height, mm | | Comment |
| --- | --- | --- | --- | --- |
| 11.6 | 001/001 | 224 | | Strong, well-defined. |
| 4.55 | 11;02 | 81 | 7 mm, w/2 | Asymmetrical |
| 3.25 | 003/004 | 57 | | Broad, symmetrical |
| 2.62 | 13;20 hk | 84 | | Band-head listed. Band extending 2.64  1.97 A, asymmetrical |
| 1.522 | 06 | 114 | 9 mm, w at h/2 | Sharp; slightly asymmetric | x 0

| d,A | Probable Index | Height, mm | | Comment |
| --- | --- | --- | --- | --- |
| 9.6 | 001 | 227 | | V.strong, well-defined, symmetrical |
| 4.55 | 11;02 | 97 mm | 8 mm, w/2 | Asymmetrical |
| 3.145 | 003 | 93 | | Moderately sharp, symm. |
| 2.51 | 13;20 | 106 | | Band (strongly asymm.) |
| 2.27 | 22;04 | 47 | | 2.64  1.97 |
| 1.522 | 06 | 120 | 8 mm, w at h/2 | Sharp, slightly asymmetric |

*Uncertain due to complications due to mixed layers.

Returning now to Example A, as already noted, and as may be seen from the details set forth in the example, the nickel occurs predominantly in the dioctahedral phase. A tabulation of x-ray data for the product of Example A is set forth in Table 5, which follows.

TABLE V $w = \frac{1}{3}$ (ca. 1 Ni per unit cell) and x = 0.8 (expectation value)

| d,A | Probable Index | Height, mm | | Comment |
| --- | --- | --- | --- | --- |
| 12.0 | 001/001 | 100 | | Ill-defined, symmetrical |
| 4.45 | 11;02 | 134 | 8 mm, w/2 | Sharp, asymmetrical |
| 3.16 | 003/004 | 35 | | Broad, slightly asymmetrical |
| 2.55 | 13;20 | 64 | | Broad, asymmetrical |
| 1.686 | 31;15;24 | 15 | | Broad, asymmetrical |
| 1.491 | 06 | 37 | 18 mm, w at h/2 | Asymmetrical on low-angle side indicating a small amount of trioctahedral component |

From size considerations alone $Ni^{2+}$ is expected to occupy octahedral sites and to be excluded from tetrahedral sites in the layer structure, or to occupy charge-balancing sites either as $Ni^{2+}$ or as a hydroxy-nickel species. $Al^{3+}$, however, can occupy octahedral, tetrahedral, or charge-balancing sites; in the latter case, a hydroxy-aluminum species is to be expected. The diffraction data in the previous tables show 06 reflections typical of mixed dioctahedral/trioctahedral minerals. Furthermore, the trioctahedral 06 (>1.505A) peak height increases, and the dioctahedral 06 (>1.505A) peak height decreases, as the overall average Ni per unit cell varies over the range 0 to 6. In addition, reference is made to the attached drawing wherein the intensity of the trioctahedral 06 reflection, corrected for change in the mass absorption coefficient as Ni increases and Al decreases, is plotted as a function of the expected overall average level of Ni, i.e. the expected overall average Ni per unit cell based on feed composition. In the drawing, $h(06_{tri})$ is the 06 peak height in chart units; $\mu/\rho$ is the mass absorption coefficient and the Ni/unit cell is equal to 3w as defined in the formula given at the beginning of this specification. Note that the intensity is a linear function of Ni/u.c. and that the line extrapolates to zero intensity at zero nickel level. The line w in FIG. 1 is the best fit for the experimental points which represent values of x from 0.5 to 1.45 and values of 3w of from 0 to 6. For this particular system, any amount of nickel added (within the compositional limits) crystallizes as a trioctahedral nickel silicate which may or may not contain 4-coordinated Al. Thus, in this system, any mixture of NiO and $Al_2O_3$ which contains less than the amount of Ni required for 6 Ni/u.c. will form mixed dioctahedral-trioctahedral phases.

As already stated, one of the principal fields of utility for products made in accordance with the invention is in the field of hydrocarbon conversion, such as for example catalytic cracking. In a series of cracking experiments in which cumene was passed over samples of the inventive preparations at 350°C., the results set forth in Table 6 were obtained. In this tabulation, the first 12 entries represent cumene cracking results on various preparations made along the general lines of Examples B–E inclusive. For each sample, the values of w and of x are given, based upon the structural formulation presented earlier in this specification. The last entry in Table 6 is for a preparation made in accordance with U.S. Pat. No. 2,658,875, cited hereinabove, and which results in a lattice which is chargebalanced, as already noted, and for which accordingly x equals zero. This preparation is termed nickel montmorillonite in the patent, although I consider that a more exact term is nickel talc.

The first column of figures in Table 6 gives the percent conversion, which is the volume percent conversion of cumene to all products corrected to 100% mass balance. The latter is the ratio of the mass of total products recovered to the mass of cumene fed, multiplied by 100. The experimental figures are given in the last column of Table 6.

The catalytic apparatus used was essentially a micro device, two microliters of cumene being slugged at a flow rate of an inert carrier gas of 0.5 cubic centimeters per second. The table shows two duplicate runs, from which the excellent reproducibility of the results may be judged.

This cracking test essentially determines the ability of the catalyst to crack the aliphatic side chain from the benzene ring. That the samples in accordance with the invention were highly successful in doing this is clear from the table. Also worthy of note is the remarkably low figure for the nickel talc shown in the last line of the table; this substance had no cumene cracking activity whatsoever at the temperature employed in the test.

TABLE VI

| Description of Sample | Cumene Cracking % Conversion | Mass Balance, % |
|---|---|---|
| w = 1, x = 1.5 | 100.0 | 32.6 |
| Duplicate run | 100.0 | 31.3 |
| w = 1, x = 1.0 | 100.0 | 74.9 |
| w = 1, x = 0.5 | 96.3 | 84.5 |
| w = 1, x = 0.25 | 98.7 | 68.3 |
| w = 1, x = 0.125 | 98.6 | 73.7 |
| w = 1, x = 0.062 | 97.4 | 72.2 |
| w = 4/3, x = 1.5 | 84.0 | 81.0 |
| w = 2, x = 1.5 | 100.0 | 63.0 |
| Duplicate run | 100.0 | 71.7 |
| w = 2, x = 1.0 | 94.0 | 54.9 |
| w = 2, x = 0.5 | 100.0 | 48.7 |
| U.S. 2,658,875: w = 2, x = 0 | 0.0 | 101.8 |

The foregoing examples have illustrated the employment of nickel in the inventive aluminosilicates. Next, a group of examples will follow showing other heavy metals used in accordance with the invention.

EXAMPLE F 40 gms silicic acid (assaying 79% $SiO_2$) were dispersed in 1 liter of $H_2O$. With continued stirring, 70.8 g $AlCl_3 \cdot 6H_2O$ and 17.6 g cobalt chloride, $CoCl_2 \cdot 6H_2O$, were dissolved in the silica slurry. At this point 75 ml of aqua ammonia (29% $NH_3$) were added to precipitate the mixed hydrous oxides. The slurry was filtered and washed by redispersion and filtration through a total of three wash cycles. The filter cake was dispersed in water, 3.0 g NaOH dissolved in the dispersion, and the total volume made up to 1 liter. The pH at this point was 9.5.

The slurry was placed in a super-pressure bomb and heated, with rocking, at 285°C. for two days. The pressure was 1040 psi. After cooling, the bomb was opened and the product slurry filtered. The filter cake was washed (by redispersion and refiltration) twice with aqueous ammonia and once with water, and then dried in an oven at 110°C.

EXAMPLE G 30.35 gm of ball-milled silicic acid (79% $SiO_2$) and 6.00 gm of germanium oxide, $GeO_2$, were dispersed in 1 liter of water. With continued stirring, 55.05 g of $AlCl_3 \cdot 6H_2O$ were dissolved in this silica-germania slurry. The hydrous oxide of aluminum was then precipitated by the addition of 75 ml of aqua ammonia (29% $NH_3$). This final slurry was filtered and washed with water by redispersion and filtration through three cycles. The filter cake was redispersed in $H_2O$, 1.80 g NaOH dissolved in the mixture, and the total volume brought to 1 liter by adding additional water. The slurry was charged to a super-pressure bomb and treated, with rocking, at 285°C. and 1040 psi for 2 days. After cooling, the bomb contents were filtered and then washed, by redispersion and refiltration, twice with aqua ammonia and once with water. The final filter cake was dried in an oven at 110°C.

EXAMPLE H 40 g of ball-milled silicic acid (79% $SiO_2$) were dispersed in water and, with continued stirring, 70.8 g of $AlCl_3 \cdot 6H_2O$ and 19.72 g chromium chloride, $CrCl_3 \cdot 6H_2O$, were dissolved in the silica slurry. At this point, 75 ml of aqua ammonia (29% $NH_3$) were added to precipitate the hydrous oxides. This mixture of silica, chromia, and alumina was filtered and washed with water by redispersion and refiltration, through three cycles. The final filter cake was dispersed in water, 2.36 g of NaOH dissolved in the mixture, and the volume made up to 1 liter with additional water. The slurry was charged to the Aminco super-pressure bomb and treated at 285°C. with 1040 psi for 48 hours. After cooling, the product slurry was filtered and the cake washed twice with aqua ammonia and once with water, by the previously described redispersion technique. The final filter cake was dried in an oven at 110°C.

EXAMPLE I

In a manner similar to Example H, a product was prepared from 40 g ball-milled silicic acid (79% $SiO_2$); 70.8 g $AlCl_3 \cdot 6H_2O$; 20.19 g ferric chloride, $FeCl_3 \cdot 6H_2O$; 75 ml aqua ammonia (29% $NH_3$); 2.36 g NaOH; and sufficient water and additional ammonia to carry out the various operations.

EXAMPLE J

In a manner similar to Example F, a product was prepared from 40 g of ball-milled silicic acid (79% $SiO_2$); 70.8 g $AlCl_3 \cdot 6H_2O$; 7.52 g cupric fluoride, $CuF_2$; 75 ml aqua ammonia (29% $NH_3$); 2.36 g NaOH; and sufficient water and additional ammonia to complete the various operations.

EXAMPLE K 28.5 g $SiO_2$ (as 500 g polysilicic acid gel) were dispersed in 200 ml water and 21.6 g $Al_2O_3 \cdot 3H_2O$ (commercial Alcoa C-33 alumina trihydrate) added, with continued stirring, to give a silica-alumina slurry. 12.1 g zinc silicofluoride, $ZnSiF_6 \cdot 6H_2O$, were dissolved in 100 ml water and added to the above slurry, again with vigorous stirring. Finally, 1.03 g $NH_4F$ were dissolved in 2.5 ml $H_2O$ and added to the mixture, also with stirring. The small beaker containing the $NH_4F$ solution was rinsed into the mixture with additional water. The volume of this final mixture was brought to 1000 ml with additional water; the pH at this point was 6. 900 ml of the mixture were charged to the super-pressure bomb and treated at 300°C. and 1240 psig for two days. After cooling the product was filtered, washed with water, and dried in an oven at 110°C.

EXAMPLE L 500 g of polysilicic acid gel which contained 28.5 g $SiO_2$ were dispersed in 250 ml of water, together with 21.8 g of $Al_2O_3 \cdot 3H_2O$, (commercial Alcoa C-33 alumina trihydrate). In a separate vessel, 1.03 g $NH_4F$, 2.5 ml aqua ammonia (29% $NH_3$) and 3.53 g ammonium paratungstate were dissolved in 450 ml of water with vigorous stirring. The paratungstate was slow to dissolve and as this solution was added to the silica-alumina slurry, with stirring, it was noted that some undissolved paratungstate was present. The total volume was brought to 1350 ml with additional water (at this point the pH 9), and 1000 ml were charged to the super-pressure bomb and treated at 300°C. and 1240 psig for two days. After cooling, the product slurry pH was 7.7. The slurry was filtered, washed with water, and the filter cake dried in an oven at 110°C.

EXAMPLE M

In a manner similar to Example K, a mineral was synthesized from: 500 g polysilicic acid gel (containing 28.5 g $SiO_2$); 10.5 g magnesium silicofluoride, $MgSiF_6$; 1.03 g $NH_4F$; 2.5 ml $NH_4OH$; and sufficient water to bring final volume to 1300 ml. 1000 ml were charged to the bomb and treated hydrothermally at 300°C., for two days. The product was filtered, washed with water, and dried in an oven at 110°C.

EXAMPLES N, O, P, Q, R

These five examples constitute a series of increasing magnesium content. The manner of preparation was the same for all five examples, except for the quantities of aluminum chloride, sodium chloride, and sodium hydroxide. The procedure was as follows:

To 40 g of diatomaceous earth (Celite 521) dispersed in one liter of distilled water, there were added, with stirring, A g of $AlCl_3 \cdot 6H_2O$, and B g of $MgCl_2 \cdot 6 H_2O$. After solution was complete, 150 ml of aqua ammonia (29% $NH_3$) were added, with continued stirring, to precipitate the hydrous oxides. The resultant $SiO_2$-$Al_2O_3$-MgO slurry was filtered and washed until free of $Cl^-$ ion, redispersed in $H_2O$ to a total volume of 1 liter, and C g of NaOH, dissolved in a minimum amount of water, added with stirring. This final mixture was charged to an Aminco superpressure bomb and heated, with rocking, at 285°C. for two days. After cooling, the bomb was opened and the product slurry filtered. The filter cake was washed (by redispersion and refiltration) twice with aqueous ammonia and once with water and then dried in an oven at 110°C.

The various values of A, B, and C follow:

| Example | A, g | B, g | C, g | α, g |
|---------|------|------|------|------|
| N | 96.4 | 0 | 3.2 | 0 |
| O | 92.0 | 19.3 | 3.8 | 1 |
| P | 69.0 | 38.7 | 3.8 | 2 |
| Q | 46.0 | 58.0 | 3.8 | 3 |
| R | 23.0 | 77.4 | 3.8 | 4 |

The foregoing examples all correspond to the series:

$$7 SiO_2 : (5 - \alpha) Al(OH)_3 : \alpha MgO$$

wherein α varies from zero to 4, as given in the above tabulation.

The number of products selected from the foregoing examples were tested for catalytic cracking activity. The following tabulation shows the results of dimethylbutane cracking at 525°C.

TABLE VII

| Example | Metal | % Conv. 525°C. | $E_a$ Kcal/mole | Surface Area, $m^2/gm$ |
|---------|-------|----------------|-----------------|------------------------|
| A | Ni | * | * | 187 |
| F | Co | 30 | 22 | 156 |
| H | Cr | 57.5 | 10 | 214 |
| I | Fe | 4.3 | 32 | 96 |
| J | Cu | 46 | 18 | 173 |
| N | Al | 88 | 18.2 | 96.5 |
| O | Mg | 2.2 | 41.0 | 93.2 |
| P | Mg | 1.2 | 43 | 120 |
| Q | Mg | 1.5 | 43 | 105 |
| R | Mg | 2.5 | 45 | 174 |

*Extremely active catalyst. Products contained only C, $CH_4$, $H_2$. Nature of products put run outside the scope of the DMB method.
Note: Catalyst pretreatment did not include steam deactivation.

The succeeding tabulation shows the results of cetane cracking tests at 500°C.

TABLE VIII

| Example | Metal | % Conv. 500°C. | Gaso. Conv. | Vol $H_2$, liters STP per gm Cetane Cracked | gm Coke gm Cetane Cracked |
|---------|-------|----------------|-------------|----------------------------------------------|---------------------------|
| A | Ni | 79.5 | 0.202 | 0.410 | 0.282 |
| J | Cu | 40.6 | 0.436 | — | 0.14 |
| N | Al | 65.9 | 0.517 | 0.0055 | 0.0094 |
| O | Mg | 68.4 | 0.570 | — | 0.0500 |
| P | Mg | 34.9 | 0.896 | | |
| Q | Mg | 3.8 | 1.0 | | |
| R | Mg | 69.4 | 0.527 | | |

EXAMPLES S, T, U, V, W

These five examples constitute a series of similar preparations in which cobalt and mixtures of nickel and cobalt were included in the preparations. The general procedure was the same for all examples in this group and consisted of mixing the starting materials specified below in the proportions given, mixing thoroughly, and charging into a silver lined, 15 ml capacity stainless steel autoclave. This was sealed and heated in a furnace at 350°C. for 24 hours. At the end of this period, the autoclave was removed, quenched in cold water, and the contents removed. The product slurry was mixed with deionized water with agitation and then filtered and washed until free of chloride ion. The filter cake was dried at 60°C. overnight, ground, and studied by X-ray and infrared techniques.

The following materials were used:
A ml of 2.213 formal* $CoCl_2$ solution,
B ml of 3.085 F $NiCl_2$ solution,
C ml of 2.390 $AlCl_3$ solution,
D ml of 10.09 F (or N) NaOH solution,
(or, in some cases, E ml of 10.97 N NaOH solution),
F gms of Fisher silicic acid ($SiO_2 \cdot 0.635 H_2O$), and
G ml deionized water

*Formula weight/liter of solution; Formality × milliliters = millimoles all aqueous solutions with deionized water.

The various values of A, B, C, D, E, F, and G for the examples are given below:

| Example | A, ml | B, ml | C, ml | D, ml | E, ml | F, g | G, ml |
|---|---|---|---|---|---|---|---|
| S | 9.04 | — | 16.76 | 17.2 | — | 4.76 | 8.4 |
| T | 27.12 | — | 8.4 | 19.9 | — | 4.28 | 1.6 |
| U | 1.13 | 0.80 | 16.2 | — | 12.2 | 5.11 | 16.8 |
| V | 4.52 | 3.22 | 16.76 | — | 17.2 | 5.23 | 5.9 |
| W | 13.6 | 9.65 | 8.4 | — | 18.2 | 4.71 | 1.6 |

Structural investigations by X-ray diffraction and infrared spectroscopy gave the following results for the products obtained:

TABLE IX

| Ex. | Co/u.c. | Ni/u.c. | x | 001 spacing, A | 06 spacing trioct., A | Wt Fac. | 06 Sp. dioct., A | Wt. Fac. |
|---|---|---|---|---|---|---|---|---|
| S | 2 | nil | 4/3 | 14.5 | 1.531 | 390 | 1.495 | 320 |
| T | 6 | nil | 2 | 14.7 | 1.538 | 1090 | n.p.* | — |
| U | 0.25 | 0.25 | 1/3 | 11.2 | n.p. | — | 1.488 | 680 |
| V | 1 | 1 | 4/3 | 12.6 | 1.526 | 410 | 1.489 | 260 |
| W | 3 | 3 | 2 | 13.2 | 1.531 | 1220 | n.p. | — |

*n.p.: not present.

In Table IX, the second and third columns give the number of atoms of cobalt and nickel respectively per unit cell. The value of $x$ given refers to the general structural formula given near the beginning of this specification. The 001 spacing was determined by X-ray diffraction, and the trioctahedral and dioctahedral 06 spacings were likewise thus determined. The weight factor expresses the relative preponderance of the two phases.

It will be helpful to outline a procedure by which it may be determined if a given preparation falls within the scope of the inventive compositions, with particular reference to the formulation set forth hereinabove and in the claims.

First, x-ray diffraction must establish the material in question to be a 2:1 layer silicate by procedures well known to those skilled in the art. Of particular help in this instance would be pertinent subject matter in the text by G. Brown, cited hereinabove. The material being examined should be substantially free of accessory phases.

It is then necessary to obtain a total analysis of the sample, expressed as the oxides of the cations in their original oxidation states. Suitable analytical methods are discussed in Furman, N.H., Ed. "Scott's Standard Methods of Chemical Analysis", 6th Ed. Van Nostrand, New York (1962), Vol. I, Chapter 41. If fluoride is present the percent oxides plus percent fluoride is corrected by subtracting the percentage of fluoride ion multiplied by the quotient of the equivalent weight of oxygen ion divided by the equivalent weight of fluoride ion. Adequacy of the analysis is indicated if this corrected total lies between 99.5% and 100.5%. The analysis is recalculated as charge equivalents (i.e., cation equivalents $x$ cation charge), normalized to charges per 44 charges (the negative charge per unit cell of the oxygen-hydroxyl framework of the 2:1 layer silicates) and finally expressed as cations per unit cell (e.g., the silicon charges per 44 charges divided by the charge of the silicon cation). These cations are then distributed over the tetrahedral and octahedral layers in accord with the tabulated lists of cations falling into the categories G, Y, Q, and R. In this way the values of the various subscripts in the general formula can be obtained. Examples of this technique, a statement of the rules for cation distribution, and a discussion of the uncertainties involved and the meaning of the results can be found in Kelly, W.P., "Interpretation of chemical analyses of clays", Clays and Clay Technology, Bulletin 169 of the California Division of Mines (1955), pp. 92–94; and Osthaus, B.B., "Interpretation of chemical analyses of montmorillonite", same reference, pp. 95–100.

An illustrative example follows. This particular example has been selected to include the complexities arising from mixed di- and trioctahedral phases, mixed 1:1 and 3:2 substitution octahedrally, and mixed 4- and 6-fold coordinated aluminum ion.

| | Analysis | Cation Equiv. | Charge Equiv. | Charges 44 Charges | Cations U.C. | Distribution |
|---|---|---|---|---|---|---|
| $SiO_2$ | 50.59 | 0.842 | 3.37 | 27.59 | 6.90 | Tet: Si, 6.90 |
| $Al_2O_3$ | 23.33 | 0.458 | 1.37 | 11.25 | 3.75 | Al, 1.10  1.10− |
| NiO | 16.86 | 0.226 | 0.451 | 3.70 | 1.85 | Oct: Al, 2.65 |
| $(NH_4)_2O$ | 4.61 | 0.177 | 0.177 | 1.45 | 1.45 | Ni, 1.85  0.35− |
| F | 2.09 | 0.110 | — | — | — | 1.45− |
| $H_2O$ | 3.41 | | | | | Interlayer: |
| | 100.89 | | 5.369 | 43.99 | | $NH_4$: 1.45  1.45+ |
| F ≡ O Corr. | − 0.88 | | | | | |
| Total | 100.01 | | | | | |

From the tabulated calculation, $x$ in the general formula is 1.10, $3w$ is 1.85, and $ew = 4 − 2.65 = 1.35$, so that $e = 2.19$. The value of $f$ can be obtained by noting that $F/Si = f/(8-x) = 0.131$. Since $x = 1.10, f = 0.90$. The coefficient, $d$, of the amount of exchange ion $(NH_4)$ is 1.45. Therefore, the average formula for this example is

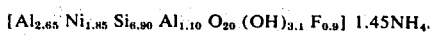

$[Al_{2.65} Ni_{1.85} Si_{6.90} Al_{1.10} O_{20} (OH)_{3.1} F_{0.9}] 1.45NH_4$.

Comparison of the inventive ranges of $x$, $e$, $w$, $f$, and $d$ and the ions which can fill the roles of G, Y, Q, R, and C with the results shown above demonstrates that the example falls within the scope of the invention.

An alternate method of calculation is based on the use of ionic ratios. However, the method is still dependent on the aluminum distribution between 4- and 6-fold states. If we define $Si/Al = R_1 = (8-x)/(4-ew+x)$; $Si/Ni = R_2 = (8-x)/3w$; $Al^{IV}/Al^{VI} = R_3$; and $F/Si = R_4 = f/(8-x)$, it can be shown that $$x = 8R_3/R_1R_3 + R_1 + R_3) \quad (1)$$

$$w = (8-x)/3R_2 \quad (2)$$

$$e = (4R_3 - x)/w\, R_3 \quad (3)$$

$$d \text{ (if exchange cation is monovalent)} = x + (e-2)3w \quad (4)$$

Once $x$ is obtained from the ratios and eq (1), $w$ can be calculated according to eq. (2), $e$ from eq (3) with $x$ and $w$; and finally $d$ from eq. (4). From the analysis given, $R_1 = 1.84$; $R_2 = 3.73$; and $R_4 = 0.131$. From the distribution given, $R_3 = 0.416$. Thus, $x = 1.10$; $w = 0.617$, $e = 2.19$, and $d = 1.45$ from equations 1 through 4, in good agreement with the values obtained by the distribution procedure. The value of $f$ can be recovered from $R_4$ as shown above. This calculation is presented simply to show the validity of equations 1 through 4. Given such validity, any analytical method or combination of methods that provides accurate values of the required ratios will give the correct values of $x$, $w$, $e$, and $d$.

From the foregoing examples, it is apparent that a general method of producing the laminar 2 : 1 layer lattice aluminosilicate mineral of this invention can be described in the following manner. To a dispersion of amorphous silica in water is added, with stirring, suitable sources of the ions G, Y, Q, and R, (note that silicon is the predominant part of Q).

Such sources are the hydrous oxides and simple inorganic and organic salts of the ions listed in the tables of ionic radii, which were presented hereinabove. If a salt is used, it is convenient, but not necessary, to choose anions which either enter lattice positions (for example, fluoride or silicofluoride) or are readily removed from the product by calcination (for example, acetate and nitrate). Alternatively, anions may be selected which result in soluble by-products which can be removed from the feed slurry or alternatively from the product by filtration and washing. However, the filtration rates of layer aluminosilicates are low and large-scale production filtration of the product is best avoided.

Once the mixture of silica and G, Y, Q, and R is obtained, within the compositional limits stated hereinabove, the appropriate amount of charge-balancing cation C is added, conveniently as the hydroxide or fluoride or mixtures of both. As stated hereinabove, C may be selected from the group consisting of alkali metal, alkaline earth metal, heavy metal, heavy metal partial hydroxy, ammonium, substituted ammonium, substituted phosphonium, and the like cations and mixtures thereof. It is preferred that C be ammonium.

This final feed mixture is then charged to a pressure vessel and heated under at least autogenous pressure at a temperature generally in the range 250°C to 350°C. In general, the time for crystallization of the product decreases with increase in temperature. However, the pressure increases with temperature and the higher temperatures require massive reaction vessels. A convenient temperature is 300°C, which in an aqueous system results in a pressure of 1240 psig. At the end of the crystallization time, the product slurry can be cooled by any convenient means (for example, discharge through a quench condenser and a throttling valve to atmospheric pressure). The product can be recovered by direct drying of the slurry if the unwanted anions present are thermally decomposable, or by filtration, washing, and drying if these anions are not thermally decomposable but are present as soluble by-products. The product can then be further treated by whatever processing is required by the intended end use. For example, the product can be exchanged to the ammonium form, dried, at for example 105°C to 180°C, and then if desired calcined, for example, at 400°C to 700°C. It then is suitable for many catalytic operations, such as hydrocarbon cracking. Of course, if the temperature during the catalytic procedure is high, for example within the exemplary calcination range just given, then calcination need not be a separate step, as it occurs automatically. For other catalytic operations, the ammonium exchange, the drying, or the calcining, or all three, may be variously omitted.

It will be understood that while I have explained the invention with the aid of numerous specific examples, nevertheless considerable variation is possible in choice of raw materials, proportions, processing conditions, and the like, within the broad scope of the invention as set forth in the claims which follow:

Having described the invention I claim:

1. A synthetic laminar 2:1 layer-lattice aluminosilicate mineral possessing an inherent negative charge balanced by cations exterior to said lattice and corresponding to the following formula for a given embodiment:

$$[(G^3_{4-ew}\, Y^2_{3w})^{VI}\, (Q^4_{8-x}\, R^3_x)^{IV}\, O_{20}\, (OH)_{4-f}F_f]\cdot[d\, C^v]$$

where $2 \leq e < 3$ $0 \leq w \leq 2$ $0 \leq ew \leq 4$ $0 \leq (e-2)w \leq \frac{1}{3}$ $0.05 \leq x < 2$ $f \leq 4$ $0.05 \leq dy \leq 2$ wherein said first bracket represents the average unit cell formulation of said layer lattice and said second bracket represents said charge balancing cations; and wherein G is selected from the class consisting of trivalent cations having an ionic radius not to exceed 0.75 A and mixtures thereof, provided that G is less than 100 mole percent Al when $w=0$;

Y is selected from the class consisting of divalent cations having an ionic radius not to exceed 0.75 A and mixtures thereof; provided that Y is less than 100 mole percent Mg when $w=2$;

Q is at least 95 mole percent silicon ions, the remainder consisting of tetravalent cations having an ionic radius not to exceed 0.64 A;

R is selected from the group consisting of trivalent cations having an ionic radius not to exceed 0.64 A and mixtures thereof; and C is at least one charge-balancing cation, with $y$ being its valence and d being the number of such cations C where:

$$dy = x+3(e-2)w.$$

2. A mineral in accordance with claim 1 wherein said G is selected from the class consisting of aluminum, chromium, cobalt, gallium, iron, manganese, and rhodium, and mixtures thereof.

3. A mineral in accordance with claim 1 wherein said Y is selected from the class consisting of beryllium, cobalt, copper, iron, magnesium, nickel, and zinc, and mixtures thereof.

4. A mineral in accordance with claim 1 wherein said remainder of Q is geranium.

5. A mineral in accordance with claim 1 wherein said R is selected from the class consisting of aluminum, cobalt, gallium, iron, chromium, and manganese, and mixtures thereof.

6. A mineral in accordance with claim 1 wherein said Y is nickel.

7. A mineral in accordance with claim 1 wherein said Y is cobalt.

8. A mineral in accordance with Claim 1 wherein said second bracket has the composition $$[a\ M^{n+}b\ Al(OH)\ _{3-z}]$$

wherein $$an+bz = dy = x+3(e-2)w$$

and M is selected from the group consisting of hydrogen, ammonium, alkali metal cations, multivalent metal cations other than aluminum, and partial hydroxides of multivalent metal cations, and $n$ is the unsatisfied valence of M.

9. A mineral in accordance with claim 1 wherein said C is selected from the group consisting of hydrogen, alkali metal, alkaline earth metal, heavy metal, heavy metal partial hydroxide ammonium, substituted ammonium, and substituted phosphonium cations and mixtures thereof.

10. The mineral in accordance with claim 1 wherein said mineral has been prepared by a process of hydrothermal synthesis.

11. The mineral in accordance with claim 8 wherein said mineral has been prepared by a process of hydrothermal synthesis.

12. The process of producing a laminar 2 : 1 layer lattice aluminosilicate mineral in accordance with Claim 1 which comprises the steps of:
preparing an aqueous mixture consisting essentially of water and compounds furnishing said G, said Y, said Q, said R, said O, said OH, said F, and said C in the approximate proportions set forth in claim 1 with selected values of the variables therein;
maintaining said aqueous mixture at a temperature of between about 280°C. and about 310°C. for a time sufficient for said mineral to form and under a pressure at least equal to the vapor pressure of said mixture at the selected temperature; and subsequently recovering said mineral.

13. The process in accordance with claim 12 wherein said G is selected from the group consisting of aluminum, chromium, manganese, iron, cobalt, gallium, rhodium, and mixtures thereof.

14. The process of producing a hydrocarbon cracking catalyst which comprises the steps of placing a mineral in accordance with claim 1 into its ammonium exchange form, and thereafter calcining said mineral.

15. The process in accordance with claim 14 in which said calcination takes place at a temperature within the range of about 400°C. to about 700°C.

* * * * *